United States Patent
King et al.

(10) Patent No.: US 9,550,028 B2
(45) Date of Patent: Jan. 24, 2017

(54) SINGLE STEP DESICCATING BEAD-IN-SYRINGE CONCENTRATING DEVICE

(71) Applicant: Biomet Biologics, LLC, Warsaw, IN (US)

(72) Inventors: William King, Warsaw, IN (US); Jennifer E. Woodell-May, Warsaw, IN (US)

(73) Assignee: Biomet Biologics, LLC., Warsaw, IN (US)

( * ) Notice: Subject to any disclaimer, the term of this patent is extended or adjusted under 35 U.S.C. 154(b) by 40 days.

(21) Appl. No.: 14/271,084

(22) Filed: May 6, 2014

(65) Prior Publication Data

US 2015/0320938 A1   Nov. 12, 2015

(51) Int. Cl.
| | | |
|---|---|---|
| A61M 5/315 | (2006.01) | |
| A61M 5/31 | (2006.01) | |
| A61B 10/02 | (2006.01) | |

(52) U.S. Cl.
CPC ........ *A61M 5/31596* (2013.01); *A61B 10/025* (2013.01); *A61B 10/0283* (2013.01); *A61M 5/3145* (2013.01); *A61B 2010/0258* (2013.01); *A61M 5/31511* (2013.01); *A61M 2202/0413* (2013.01); *A61M 2202/0443* (2013.01); *A61M 2202/062* (2013.01); *A61M 2202/09* (2013.01); *A61M 2202/10* (2013.01)

(58) Field of Classification Search
CPC ..................... A61M 2202/062; A61M 5/3145; A61M 5/31596; A61M 5/31511; A61M 2202/09; A61M 2202/0413; A61M 2202/10; A61M 2202/0443; B01F 13/002; B01F 11/0054; B01F 11/0082; B01F 7/00208; B01F 7/1695; B01F 13/0023; B05C 17/00553; B05C 17/00593; B05C 17/01; A61C 9/0026
See application file for complete search history.

(56) References Cited

U.S. PATENT DOCUMENTS

| | | | | |
|---|---|---|---|---|
| 3,606,094 A | * | 9/1971 | Mills et al. | .......... A61C 9/0026 222/145.6 |
| 3,723,244 A | | 3/1973 | Breillatt, Jr. | |
| 3,850,369 A | | 11/1974 | Bull et al. | |
| 3,897,343 A | | 7/1975 | Ayres | |

(Continued)

FOREIGN PATENT DOCUMENTS

| | | |
|---|---|---|
| EP | 0244834 A2 | 11/1987 |
| EP | 1079224 A2 | 2/2001 |

(Continued)

OTHER PUBLICATIONS

Merriam-Webster, Inc, Slit Defintiion, 2015.*

(Continued)

*Primary Examiner* — Quynh-Nhu H Vu
(74) *Attorney, Agent, or Firm* — Schwegman Lundberg & Woessner, P.A.

(57) ABSTRACT

A device for processing a biological material is disclosed. The device includes a syringe barrel comprising beads, a filter positioned at a close end of the barrel, a plunger insertable into the barrel through an open end, and a needle. The plunger includes a paddle assembly that is configured to mix a biological material with the beads after the biological material has been harvested from a patient.

22 Claims, 6 Drawing Sheets

(56) References Cited

U.S. PATENT DOCUMENTS

| | | |
|---|---|---|
| 3,909,419 A | 9/1975 | Ayres |
| 3,931,010 A | 1/1976 | Ayres et al. |
| 3,931,018 A | 1/1976 | North, Jr. |
| 3,982,691 A | 9/1976 | Schlutz |
| 4,046,699 A | 9/1977 | Zine, Jr. |
| 4,055,501 A | 10/1977 | Cornell |
| 4,077,396 A | 3/1978 | Wardlaw et al. |
| 4,154,690 A | 5/1979 | Ballies et al. |
| 4,187,979 A | 2/1980 | Cullis et al. |
| 4,322,298 A | 3/1982 | Persidsky |
| 4,379,849 A | 4/1983 | Heimreid |
| 4,416,654 A | 11/1983 | Schoendorfer et al. |
| 4,464,167 A | 8/1984 | Schoendorfer et al. |
| 4,572,210 A * | 2/1986 | McKinnon .......... A61M 5/3145 600/578 |
| 4,675,117 A | 6/1987 | Neumann et al. |
| 4,714,457 A | 12/1987 | Alterbaum |
| 4,776,964 A | 10/1988 | Schoendorfer et al. |
| 4,818,386 A | 4/1989 | Burns |
| 5,019,243 A | 5/1991 | McEwen et al. |
| 5,053,127 A | 10/1991 | Schoendorfer et al. |
| 5,131,907 A | 7/1992 | Williams et al. |
| 5,141,645 A | 8/1992 | Shiraki et al. |
| 5,147,290 A | 9/1992 | Jonsson et al. |
| 5,165,938 A | 11/1992 | Knighton |
| 5,171,456 A | 12/1992 | Hwang et al. |
| 5,185,001 A | 2/1993 | Galanakis |
| 5,234,608 A | 8/1993 | Duff |
| 5,269,927 A | 12/1993 | Fiehler |
| 5,271,852 A | 12/1993 | Luoma, II |
| 5,318,782 A | 6/1994 | Weis-Fogh et al. |
| 5,322,620 A | 6/1994 | Brown et al. |
| 5,344,752 A | 9/1994 | Murphy |
| 5,356,393 A * | 10/1994 | Haber .................. A61M 5/002 604/222 |
| 5,370,802 A | 12/1994 | Brown |
| 5,376,263 A | 12/1994 | Fischel |
| 5,387,187 A | 2/1995 | Fell et al. |
| 5,403,272 A | 4/1995 | Deniega et al. |
| 5,456,885 A | 10/1995 | Coleman et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,549,683 A | 8/1996 | Bonutti |
| 5,560,830 A | 10/1996 | Coleman et al. |
| 5,585,007 A | 12/1996 | Antanavich et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,895 A | 5/1997 | Tsukagoshi et al. |
| 5,632,905 A | 5/1997 | Haynes |
| 5,649,903 A | 7/1997 | Deniega et al. |
| 5,707,331 A | 1/1998 | Wells et al. |
| 5,707,876 A | 1/1998 | Levine |
| 5,733,466 A | 3/1998 | Benebo et al. |
| 5,733,545 A | 3/1998 | Hood, III |
| 5,788,662 A | 8/1998 | Antanavich et al. |
| 5,795,571 A | 8/1998 | Cederholm-Williams et al. |
| 5,795,751 A | 8/1998 | Apel |
| 5,817,519 A | 10/1998 | Zelmanovic et al. |
| 5,833,866 A | 11/1998 | Brown |
| 5,834,418 A | 11/1998 | Brazeau et al. |
| 5,837,150 A | 11/1998 | Langley et al. |
| 5,863,892 A | 1/1999 | Stern et al. |
| 5,865,785 A | 2/1999 | Bischof |
| 5,899,874 A | 5/1999 | Jonsson et al. |
| 5,900,245 A | 5/1999 | Sawhney et al. |
| 5,934,803 A | 8/1999 | Hutter |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,980,734 A | 11/1999 | Itoh et al. |
| 6,010,627 A | 1/2000 | Hood, III |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,274,090 B1 | 8/2001 | Coelho et al. |
| 6,280,400 B1 | 8/2001 | Niermann |
| 6,296,602 B1 | 10/2001 | Headley |
| 6,309,372 B1 * | 10/2001 | Fischer .................. A61O 5/062 433/90 |
| 6,368,298 B1 | 4/2002 | Beretta et al. |
| 6,417,004 B1 | 7/2002 | Brady et al. |
| 6,444,228 B1 | 9/2002 | Baugh et al. |
| 6,472,162 B1 | 10/2002 | Coelho et al. |
| 6,516,953 B1 | 2/2003 | DiCesare et al. |
| 6,592,247 B1 * | 7/2003 | Brown ............... A61B 17/8825 366/139 |
| 6,596,180 B2 | 7/2003 | Baugh et al. |
| 6,719,901 B2 | 4/2004 | Dolecek et al. |
| 6,733,471 B1 | 5/2004 | Ericson et al. |
| 6,890,728 B2 | 5/2005 | Dolecek et al. |
| 6,905,612 B2 * | 6/2005 | Dorian .................. B01D 15/02 210/219 |
| 7,179,391 B2 | 2/2007 | Leach et al. |
| 7,553,413 B2 | 6/2009 | Dorian et al. |
| 7,694,828 B2 | 4/2010 | Swift et al. |
| 8,308,681 B2 * | 11/2012 | Slocum ............ A61B 17/00491 604/82 |
| 8,317,800 B2 * | 11/2012 | Johnson ............. A61B 17/8827 366/252 |
| 8,394,068 B2 * | 3/2013 | Kosinski ............ A61M 5/31511 604/187 |
| 8,551,344 B2 | 10/2013 | Swift et al. |
| 8,753,690 B2 | 6/2014 | Higgins et al. |
| 2002/0090711 A1 | 7/2002 | Karlsson |
| 2002/0114775 A1 | 8/2002 | Pathak |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2003/0003055 A1 * | 1/2003 | Unger .................... A61K 9/127 424/9.51 |
| 2003/0198687 A1 | 10/2003 | Bennett et al. |
| 2004/0120942 A1 | 6/2004 | McGinnis et al. |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0109716 A1 | 5/2005 | Leach et al. |
| 2005/0233460 A1 | 10/2005 | Clague et al. |
| 2006/0009855 A1 | 1/2006 | Goble et al. |
| 2006/0175268 A1 | 8/2006 | Dorian et al. |
| 2006/0243676 A1 | 11/2006 | Swift et al. |
| 2006/0264824 A1 * | 11/2006 | Swisher, III ........ A61M 5/3129 604/110 |
| 2009/0112157 A1 * | 4/2009 | Jessop .................... A61C 5/068 604/91 |
| 2009/0220482 A1 | 9/2009 | Higgins et al. |
| 2009/0236297 A1 | 9/2009 | Dorian et al. |
| 2010/0198130 A1 | 8/2010 | Swift et al. |
| 2011/0301496 A1 * | 12/2011 | Lampropoulos ... A61B 10/0283 600/562 |

(56) References Cited

U.S. PATENT DOCUMENTS

2012/0008455 A1*  1/2012  Sand .................. A61B 17/8833
                                                            366/130
2014/0034567 A1   2/2014  Swift et al.
2014/0242045 A1   8/2014  Higgins et al.

FOREIGN PATENT DOCUMENTS

| EP | 1381410 A2 | 1/2004 |
| EP | 1716901 A1 | 11/2006 |
| EP | 1848474 A2 | 10/2007 |
| JP | 2004536794 A | 12/2004 |
| WO | WO-9812274 A1 | 3/1998 |
| WO | WO-9967277 A1 | 12/1999 |
| WO | WO-0238610 A1 | 5/2002 |
| WO | WO-02060925 A1 | 8/2002 |
| WO | WO-02081007 A2 | 10/2002 |
| WO | WO-03/099412 A1 | 12/2003 |
| WO | WO-2004009207 A1 | 1/2004 |
| WO | WO-2015171604 A1 | 11/2015 |

OTHER PUBLICATIONS

Merriam-Webster, Inc, Notch Defintiion, 2015.*
European Search Report completed on Aug. 24, 2006 for EP06242170 claiming benefit of U.S. Appl. No. 11/116,153, filed Apr. 27, 2005.
Fibrostik™ Plasma Concentrator, Attention Operating Surgeon, Cell Factor Technologies, Inc., Jul. 2003 (2 pages).
"International Application Serial No. PCT/US2015/029231, International Search Report mailed Jul. 20, 2015", 5 pgs.
"International Application Serial No. PCT/US2015/029231 , Written Opinion mailed Jul. 20, 2015", 7 pgs.

* cited by examiner

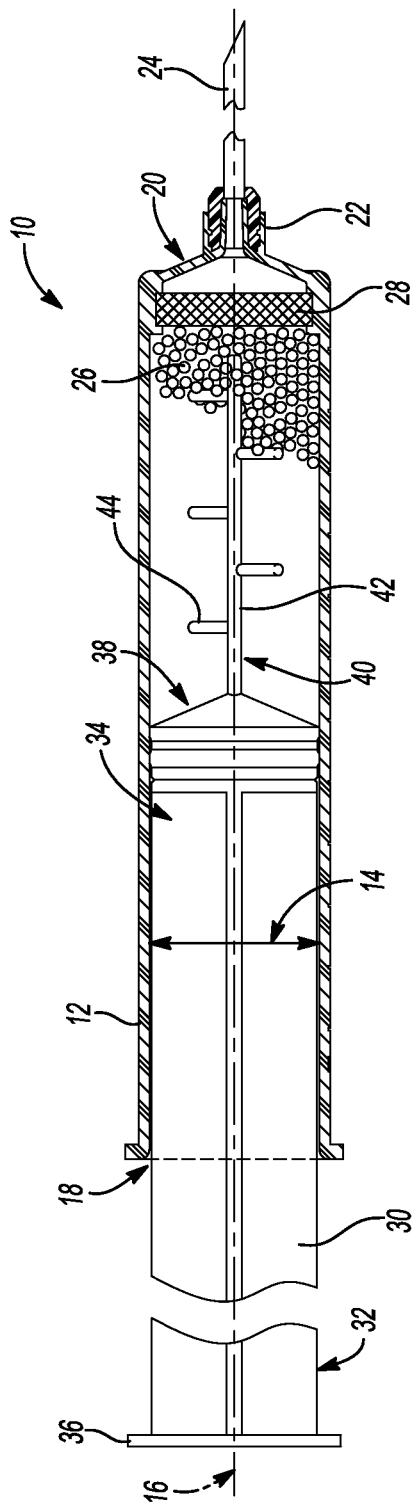
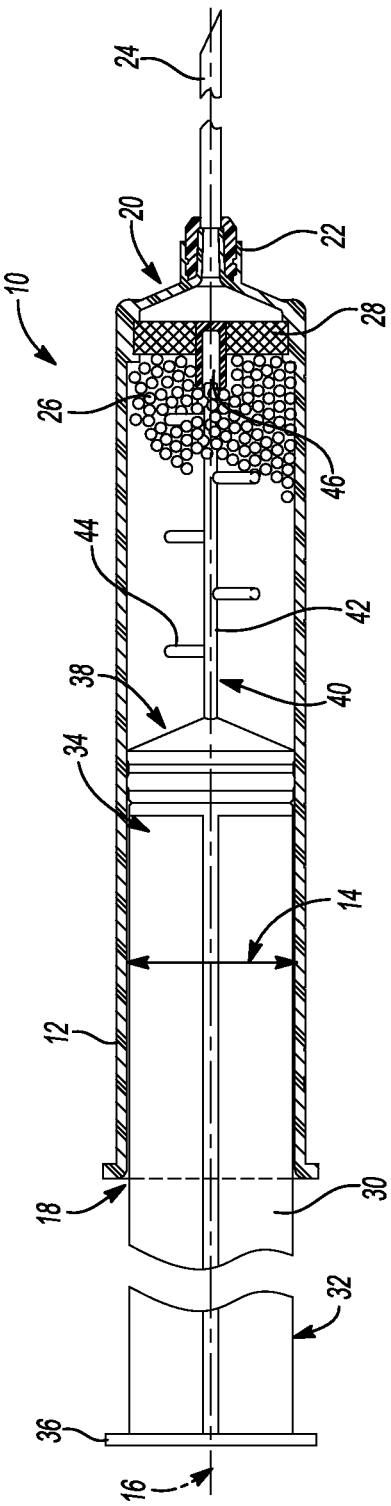
Fig-1
Fig-2

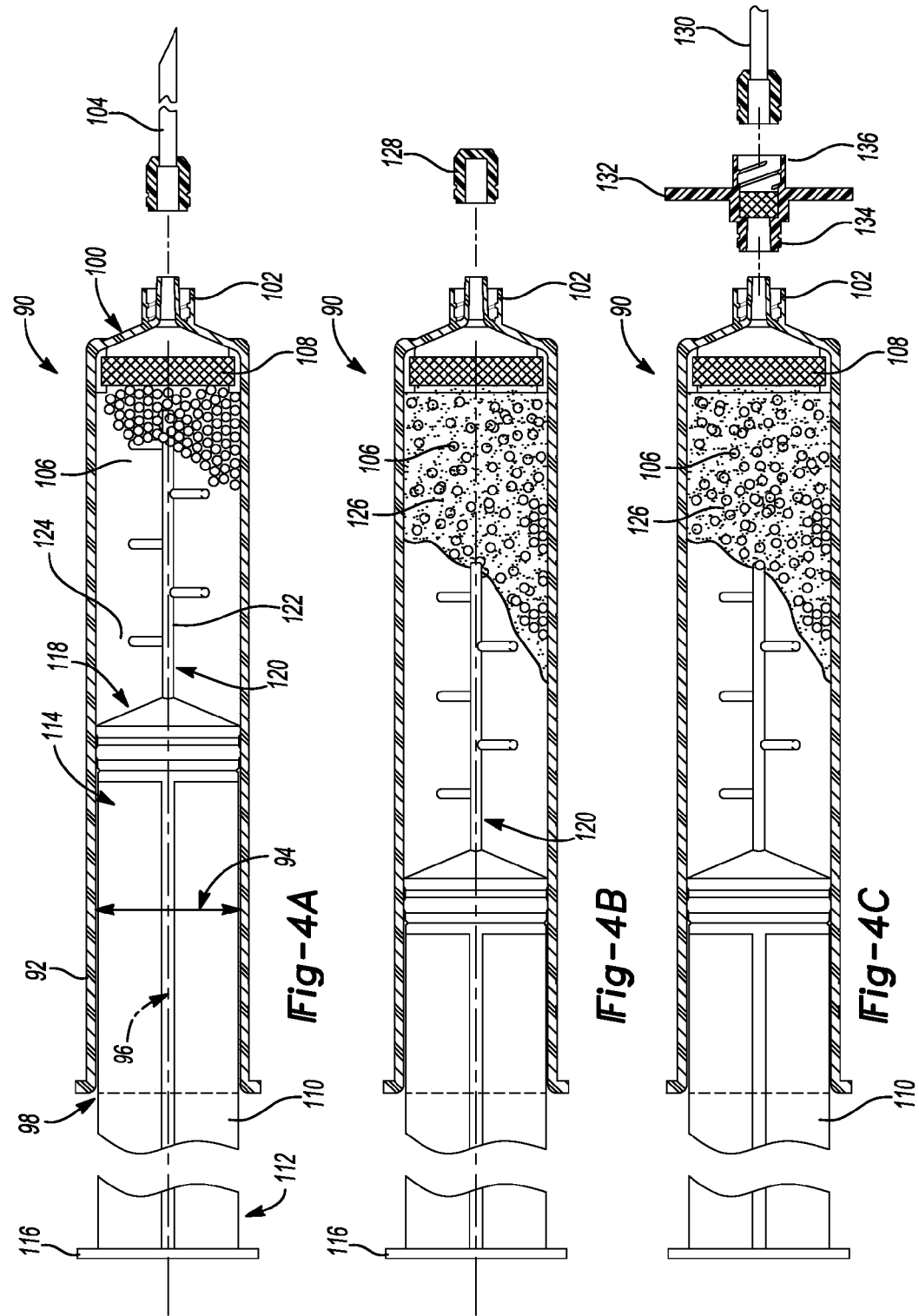

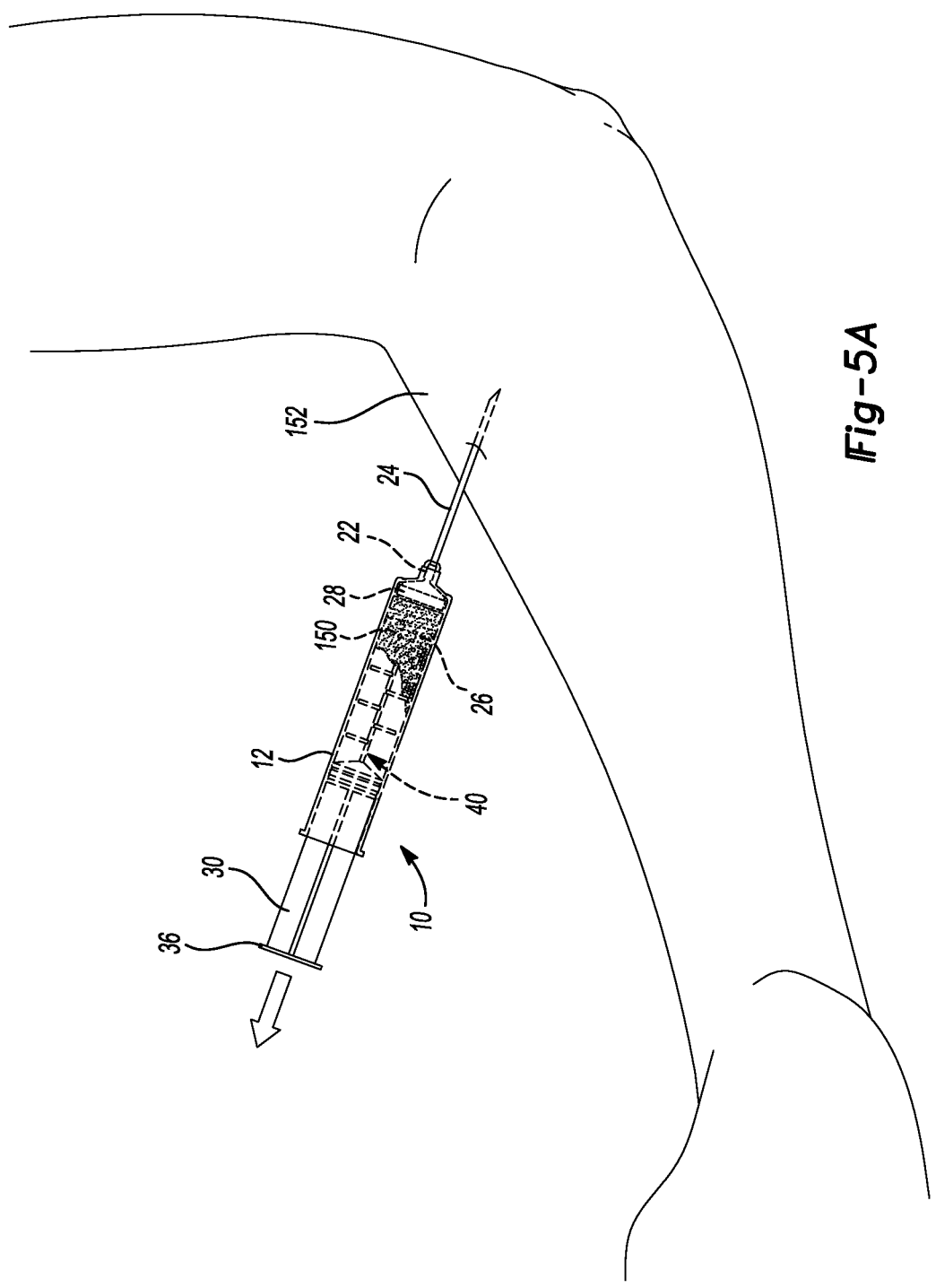

SINGLE STEP DESICCATING BEAD-IN-SYRINGE CONCENTRATING DEVICE

BACKGROUND

This section provides background information related to the present disclosure which is not necessarily prior art.

Biological materials are routinely processed in order to enhance various properties or characteristics of the biological materials. For example, whole blood is often harvested from a patient or retrieved from a blood bank, and fractionated. The whole blood can be fractionated into a red blood cell concentrate, platelet-rich plasma, platelet-poor plasma, or an autologous protein solution. Likewise, bone marrow aspirate is often harvested and processed to generated concentrated bone marrow aspirate. The type of biological material being processed and the type of processing to be performed depend on individual patients and the conditions being treated.

Although biological materials are routinely processed, the devices used to process the materials are usually complex, costly, and require elaborate processing schemes. Such devices are often bulky and the processing schemes typically require multiple processing steps, which typically include centrifugations. Often, multiple centrifugation steps are necessary in order for a medical practitioner to arrive at the desired product. The centrifugation steps are timely and can result in product loss when isolating fractions.

Therefore, there is currently a need for new devices for processing biological materials that are cost effective, easy to use, and that require fewer processing steps than currently available devices.

SUMMARY

This section provides a general summary of the disclosure, and is not a comprehensive disclosure of its full scope or all of its features.

The present technology provides a device for processing a biological material. The device comprises a syringe barrel having an inner diameter about a longitudinal axis, an open end, a closed end, and an outlet at the closed end. Desiccating beads are positioned within the barrel. The device further comprises a filter positioned at the closed end of the barrel, a plunger comprising a paddle assembly insertable into the barrel though the open end, and a needle. The filter comprises pores with diameters smaller than a diameter of the beads, but larger than a diameter of the biological material. The paddle assembly is configured to mix the biological material with the desiccating beads.

The present technology also provides for a device for processing a biological material comprising a syringe barrel having an inner diameter about a longitudinal axis from an open end to a closed end, and having an outlet at the closed end, wherein polyacrylamide beads are positioned within the barrel. A filter positioned at the closed end of the barrel, wherein the filter allows biological materials to pass through, but not the polyacrylamide beads. The device also has a plunger insertable into the barrel through the open end, the plunger having a paddle assembly, wherein the paddle assembly comprises a stem that extends along the longitudinal axis of the barrel and a plurality of paddles that extend radially from the stem. The device also has a needle. The device is configured to aspirate a biological material from a patient, process the biological material, and return the processed biological material back to the patient.

The present technology additionally provides for a method for processing a biological material. The method comprises aspirating a biological material from a patient, through a filter, and into a syringe assembly, the syringe assembly having a needle, a barrel, the filter, and a plunger, wherein a plurality of beads are positioned within the barrel, and wherein the plunger comprises a paddle assembly. The method further comprises turning a knob on the plunger, whereby the paddle assembly turns to mix the beads with the biological material to yield a processed biological material.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a cross-sectional view of a device for processing a biological material;

FIG. 2 is a cross-sectional view of a device for processing a biological material, wherein a filter of the device comprises a slit for accepting a stem of a paddle assembly;

Figure 5B:
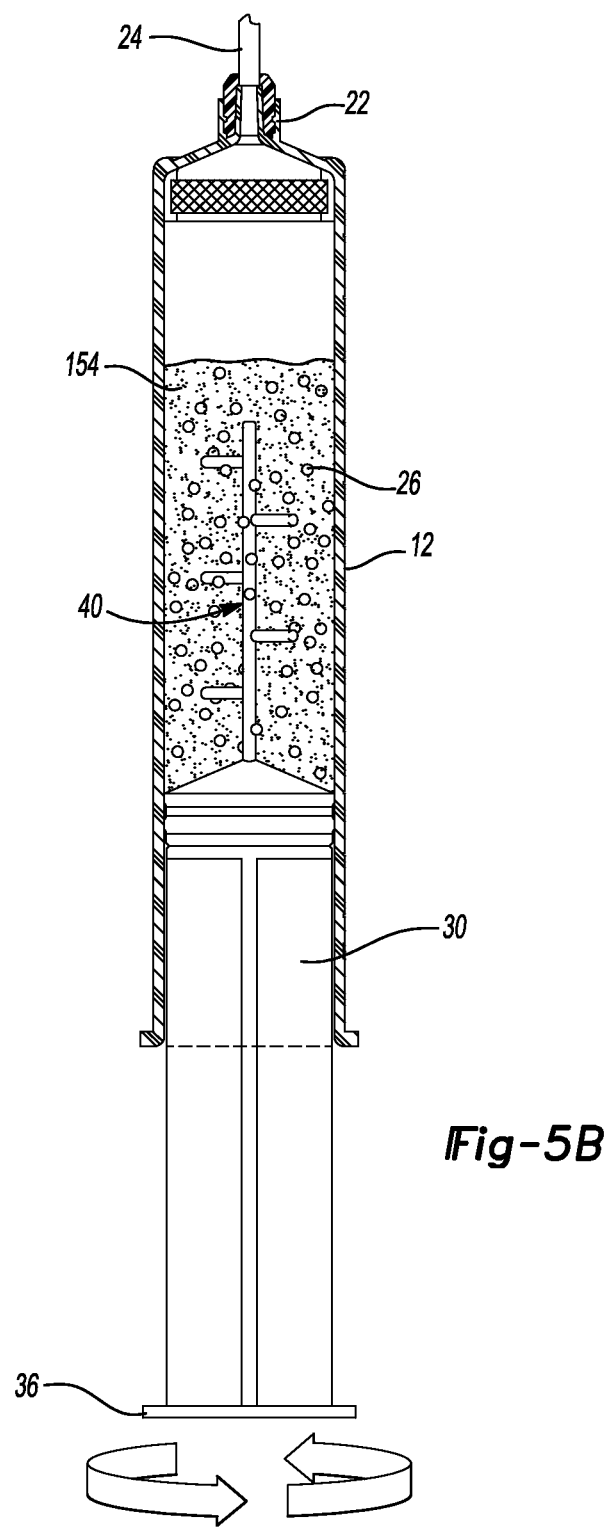
Figure 5C:
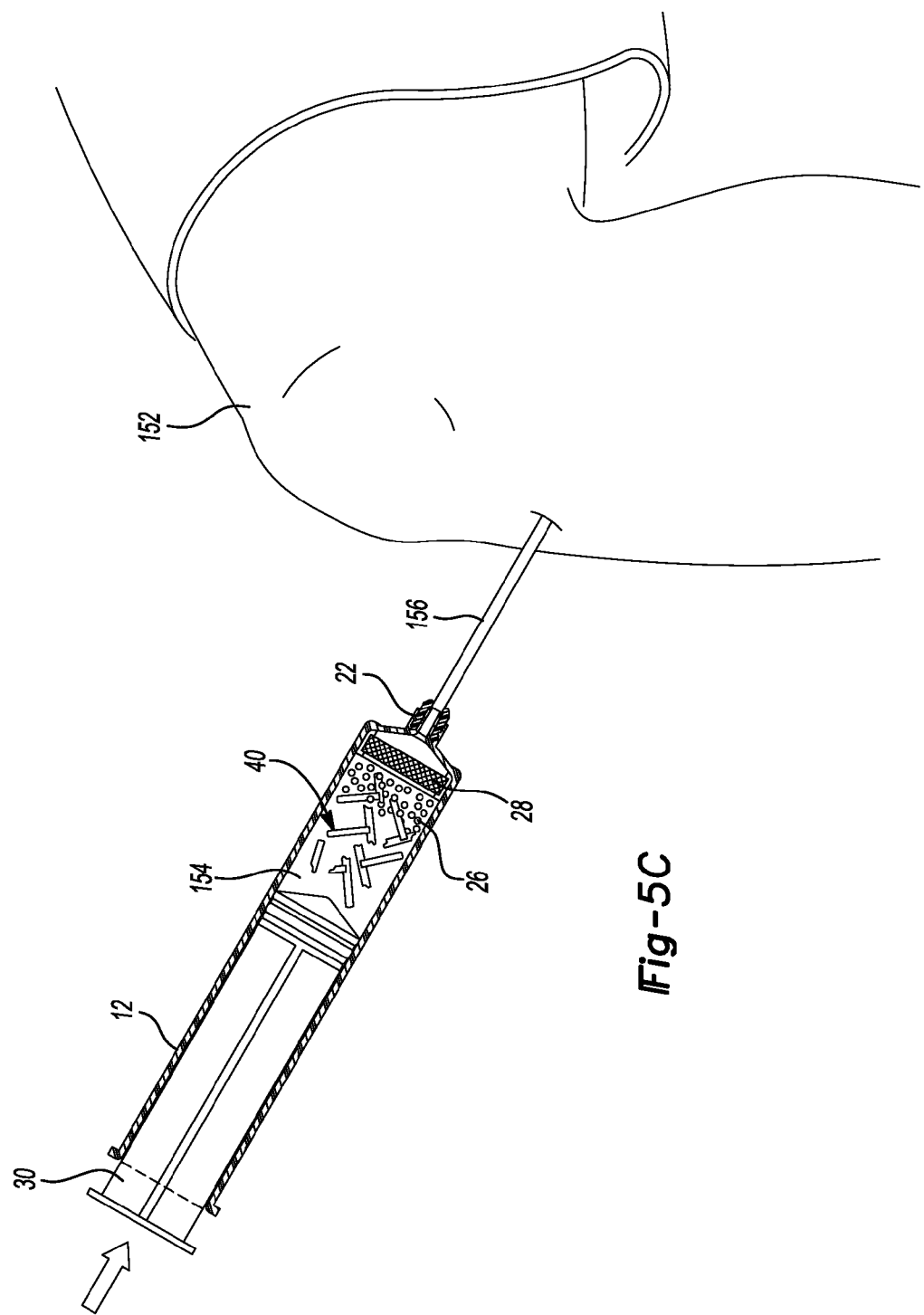

FIGS. 4A-4C are cross sectional views of a device for processing a biological material (FIG. 4A) prior to aspirating biological material; (FIG. 4B) after biological material has been harvested from a patient; and (FIG. 4C) after the biological material has been processed; and FIGS. 5A-5C provides diagrammatic illustrations of a method for using a device for processing a biological material, wherein (FIG. 5A) biological material is being aspirated into the device; (FIG. 5B) the biological material is being processed in the device; and (FIG. 5C) the processed biological material is being administered to the patient.

Corresponding reference numerals indicate corresponding parts throughout the several views of the drawings.

DETAILED DESCRIPTION

Example embodiments will now be described more fully with reference to the accompanying drawings The present technology generally provides devices and methods for processing a biological material. The device draws a biological material from a patient, and processes the biological material. The processed biological material is then administered to the patient or combined with a graft material or implant. The patient can be a human or a non-human mammal, such as a dog, cat, or horse. Accordingly, methods include processing a biological material from a patient in a device according to the current disclosure to generate a processed biological material, and administering the processed biological material to the patient.

The devices comprise beads, which are used to process biological material. The beads can comprise any suitable material for processing the biological material. The beads can be a material comprising various polymers, metals, ceramics, or glasses. In some embodiments, the beads comprise a hygroscopic material. Examples of suitable materials include glasses, minerals, polymers, metals, and polysaccharides. Minerals include corundum and quartz. Polymers include polystyrene, polyethylene, polyvinyl chloride, polypropylene, and polyacrylamide. Metals include titanium. Polysaccharides include dextran and agarose. A preferred material comprises, or consists essentially of, polyacrylamide. Preferably, the beads comprise a desiccating material. In various embodiments, the beads are conjugated with an activating material, such as an antibody. Immunoglobulin g is a non-limiting example of such an antibody.

The beads can concentrate the biological material, induce a phenotypic change in the biological material, or both. Therefore, the size and composition of the beads can be altered based on the biological material to be processed and the application. Non-limiting examples of biological material include whole blood, bone marrow, adipose tissue, and chondrocytes. The biological material is processed in the device to generate processed biological materials, such as concentrated blood, platelet-poor plasma, platelet-rich plasma, autologous protein solution, concentrated bone marrow, concentrated adipose tissue, concentrated chondrocytes, and M2 macrophages. For example, when macrophages in whole blood contact polyacrylamide beads, the polyacrylamide beads induce the macrophages to polarize into the M2 phenotype.

Devices according to the current technology can be used for a variety of applications. For example, the devices can be used in the treatment of inflammation, osteoarthritis, microfractures, meniscus implants, meniscus transplants, or other orthopedic implants or transplants. Uses further include treating osteolysis resulting from wear debris and inflammation at the site of an artificial joint in a patient. The device can be used for a laparoscopic preparation of, for example, an autologous protein solution, concentrated bone marrow aspirate, or platelet-rich plasma.

With reference to FIG. 1, a device 10 for processing a biological material comprises a syringe barrel 12 having an inner diameter 14 symetrical about a longitudinal axis 16, an open end 18, a closed end 20, and an outlet 22 at the closed end 20. A needle 24 is coupled to the outlet 22 at the closed end 20. The needle 24 can be coupled to the outlet 22 by any means commonly used in the art, such as by luer fit or interference fit. Desiccating beads 26 are positioned within the barrel 12. The desiccating beads 26 comprise any suitable desiccating material. Non-limiting examples of desiccating materials include polystyrene, polyacrylamide, glass, or metal. In an embodiment, the beads 26 comprise polyacrylamide.

The device further comprises a filter 28 that comprises pores with diameters smaller than a diameter of the beads 26, but larger than a diameter of the biological material. The filter 28 can be positioned within the barrel 12, at the closed end 20.

The device 10 further comprises a plunger 30 that is partially inserted into the barrel 12 through the open end 18. Accordingly, the plunger 30 has an exterior portion 32 and an interior portion 34. The plunger 30 has a diameter substantially similar to the inner diameter 14 of the barrel 12. The exterior portion 32 of the plunger 30 comprises a knob 36. The interior portion 34 of the plunger 30 has an end 38, which is coupled to a paddle assembly 40. As shown in FIG. 1, the end 38 can be conical. However, in other embodiments, the end 38 can be curved or flat. The paddle assembly 40 comprises a longitudinally extending stem 42 that extends along the longitudinal axis 16 of the barrel 12 and a plurality of radially extending paddles 44 that extend perpendicularly and radially about the stem 42. The paddles 44 have a length such that two opposed paddles 44 at the stem 42 have a combined transverse length that is substantially similar to the inner diameter 14 of the barrel 12. The paddle assembly 40 is axially and rotationally fixed to the plunger 30, so that turning the knob 36 causes the entire plunger 30 to turn, including the paddle assembly 40. As shown in FIG. 2, in some embodiments, the filter 28 comprises a recess or a slit 46 that is configured to receive an end of the stem 42 of the paddle assembly 40 when the plunger 30 is depressed. Whether the recess or slit 46 is present or not present, the paddle assembly 40 is configured to collapse or break into a plurality of pieces when the plunger 30 is depressed and the paddle assembly 40 is compressed between the end 38 of the plunger 30 and the filter 28. In various embodiments, the stem 42 of the paddle assembly 40 has at least one notch, slit, or section that is weaker than the rest of the stem 42, which facilitates collapsing or breaking. The paddle assembly 40 can be composed of any non-ductile material commonly used in the art. Non-ductile materials ensure that the paddle assembly 40 will break cleanly and easily. For example, the paddle assembly 40 can be composed of acrylic-based polymers. In one embodiment, the paddle assembly 40 is composed of CYROLITE® acrylic-based polymer from Evonik Cyro LLC (Parsippany, N.J.).

The device 10 is used to withdraw biological material from a patient by inserting the needle 24 into the patient and drawing back on the plunger 30. The biological material is then processed by incubating the biological material with the beads 26 and turning knob 36 to mix the biological material and the beads 26 with the paddle assembly 40. The processed biological material can then be administered to the patient by utilizing the needle 24 or replacing the needle 24 with a new, sterile needle, inserting the needle 24 or new needle into the patient, and depressing the plunger 30 until a desired volume of the processed biological material has been administered into the patient. Depressing the plunger 30 causes the paddle assembly 40 to become compressed between the end 38 of the plunger 30 and the filter 28. This results in the paddle assembly 40 collapsing or breaking so that the plunger 30 can be depressed further. Alternatively, the processed biological material is combined with a graft material or with an implant.

Figure 3:
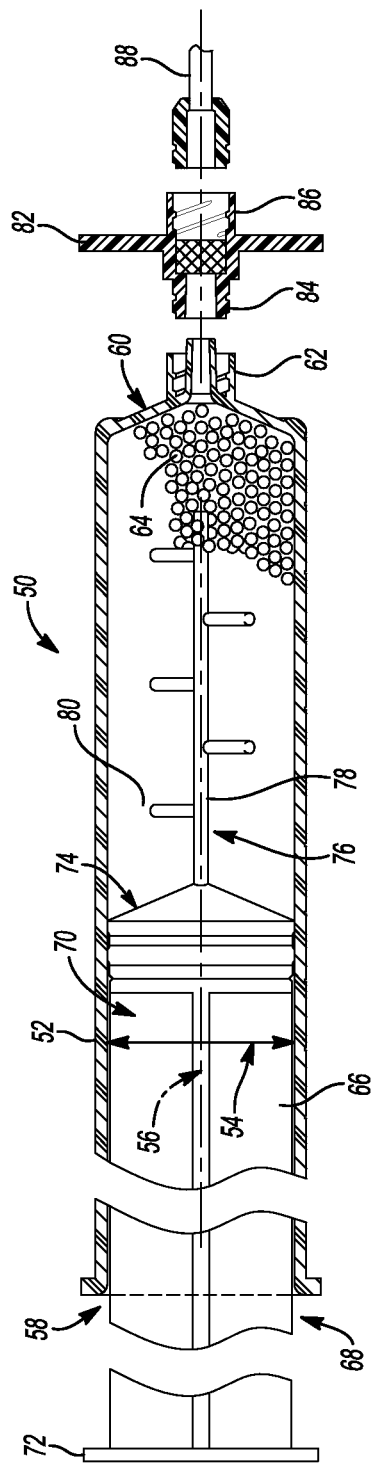
FIG. 3 is a cross-sectional view of a device for processing a biological material, wherein a filter is coupled to a syringe barrel.

FIG. 3 shows an alternative device 50 for processing a biological material. The device 50 comprises a syringe barrel 52 having an inner diameter 54 symetrical about a longitudinal axis 56, an open end 58, a closed end 60, and an outlet 62 at the closed end 60. Desiccating beads 64 are positioned within the barrel 52. The desiccating beads 64 comprise any suitable desiccating material. Non-limiting examples of desiccating materials include polystyrene, polyacrylamide, glass, or metal. In a preferred embodiment, the beads 64 comprise polyacrylamide.

The device 50 further comprises a plunger 66 that is partially inserted into the barrel 52 through the open end 58. Accordingly, the plunger 66 has an exterior portion 68 and an interior portion 70. The plunger 66 has a diameter substantially similar to the inner diameter 54 of the barrel 52. The exterior portion 68 of the plunger 66 comprises a knob 72. The interior portion 70 of the plunger 66 has an end 74, which is coupled to a paddle assembly 76. As shown in FIG. 3, the end 74 can be conical. However, in other embodiments, the end 74 can be curved or flat. The paddle assembly 76 comprises a longitudinally extending stem 78 that extends along the longitudinal axis 56 of the barrel 52 and a plurality of radially extending paddles 80 that extend perpendicularly and radially about the stem 78. The paddles 80 have a length such that the two opposed paddles 80 at the stein 78 have a combined transitory length that is substantially similar to the inner diameter 54 of the barrel 52. The paddle assembly 76 is axially and rotationally fixed to the plunger 66 so that turning the knob 72 causes the entire plunger 66 to turn, including the attached paddle assembly 76. The paddle assembly 76 is configured to collapse or break into the plurality of pieces when the plunger 66 is depressed and the paddle assembly 76 is compressed between the end 74 of the plunger 66 and the closed end 60 of the barrel 52. In various embodiments, the stem 78 of the paddle assembly 76 has at least one notch, slit, or section that is weaker than the rest of the stem 78, which facilitates collasping or breaking. By collapsing or breaking, the plunger 66 can be depressed further.

The device 50 further comprises a removable filter 82 comprising a syringe-coupling port 84 and a needle-coupling port 86 opposite the syringe-coupling port. The syringe-coupling port 84 couples the filter 82 to the barrel 52 and the needle-coupling port 86 couples the filter 82 to a needle 88. The filter 82 comprises pores that are smaller than a diameter of the beads 64, but larger than a diameter of the biological material to be processed. Therefore, the filter 82 can be selectively chosen from a plurality of filters with differing pore sizes based on the size of the biological material to be processed as long as the pore size is smaller than the diameter of the beads 64. For example, various filters can exclude platelets, leukocytes, or red blood cells from whole blood. The device 50 is used to withdraw a biological material from a patient, process the biological material, and either to administer the processed biological material to the patient or to combine the processed biological material with a graft material or implant.

FIGS. 4A-4C show a system comprising another device 90 similar to device 10 of FIG. 1, for processing a biological material. The device 90 comprises a syringe barrel 92 having an inner diameter 94 symetrical about a longitudinal axis 96, an open end 98, a closed end 100, and an outlet 102 at the closed end 100. A needle 104 is coupled to the outlet 102 at the closed end 100. The needle 104 can be coupled to the outlet 102 by any means commonly used in the art, such as by luer fit or interference fit. Desiccating beads 106 are positioned within the barrel 92. The desiccating beads 106 comprise any suitable desiccating material. Non-limiting examples of desiccating materials include polystyrene, polyacrylamide, glass, or metal. In a preferred embodiment, the beads 106 comprise polyacrylamide.

The device 90 further comprises a filter 108 that comprises pores with diameters smaller than a diameter of the beads 106, but larger than a diameter of the biological material. The filter 108 can be positioned within the barrel 92, at the closed end 100.

The device 90 further comprises a plunger 110 that is partially inserted into the barrel 92 through the open end 98. Accordingly, the plunger 110 has an exterior portion 112 and an interior portion 114. The plunger 110 has a diameter substantially similar to the inner diameter 94 of the barrel 92. The exterior portion 112 of the plunger 110 comprises a knob 116. The interior portion 114 of the plunger 110 has an end 118, which is coupled to a paddle assembly 120. As shown in FIG. 4A, the end 118 can be conical. However, in other embodiments, the end 118 can be curved or flat. The paddle assembly 120 comprises a longitudinally extending stem 122 that extends along the longitudinal axis 96 of the barrel 92 and a plurality of radially extending paddles 124 that extend perpendicularly and radially from the stem 122. The paddles 124 have a length such that two opposed paddles 124 at the stem 122 have a combined transverse length that is substantially similar to the inner diameter 94 of the barrel 92. The paddle assembly 120 is axially and rotationally fixed to the plunger so that turning the knob 116 causes the entire plunger 110 to turn, including the paddle assembly 120. In some embodiments, the filter 108 comprises a recess or a slit that is configured to receive an end of the stem 122 of the paddle assembly 120 when the plunger 110 is depressed. Whether the recess or slit is present or not present, the paddle assembly 120 is configured to collapse or break into a plurality of pieces when the plunger 110 is depressed and the paddle assembly 120 is compressed between the end 118 of the plunger 110 and the filter 108. In various embodiments, the stem 122 of the paddle assembly 120 has at least one notch, slit, or section that is weaker than the rest of the stem 122, which facilitates collapsing or breaking.

As shown in FIG. 4B, after the plunger 110 is pulled back to draw biological material 126, which may include cells, into the barrel 92, the needle 104 can be removed from the outlet 102, and the outlet 102 can be covered with a cap 128 during processing. During processing, the cap 128 allows the biological material 126 and the beads 106 to be mixed by turning the knob 116, which turns the paddle assembly 120, without a loss of biological material 126.

After processing, the cap 128 is removed and a new needle 130 can be attached to the outlet 102, as in FIG. 4A. Alternatively, as shown in FIG. 4C, a second filter 132 comprising syringe-coupling port 134 and needle-coupling port 136 can be coupled to the outlet 102. The new needle 130 can then be coupled to the needle-coupling port 136 of the second filter 132. The second filter 132 prevents cellular material from being expelled though the new needle 130 when the plunger 110 is depressed. The second filter 132 has a pore size that is smaller than the pore size of filter 108 and the second filter 132 can be selectively chosen from a plurality of filters with differing pore sizes based on a desired cell-exclusion size. For example, the second filter 132 can be smaller than a diameter of red blood cells, but larger than a diameter of platelets. Therefore, when the biological material 126 is whole blood, and after the whole blood is contacted with the beads 106, the second filter 132 can prevent red blood cells from being expelled through the new needle 130 when the plunger 110 is depressed. Consequently, only platelet-rich plasma will be expelled through the new needle 130. If the second filter 132 has a pore size that prevents both red blood cells and platelets from passing through, then platelet-poor plasma will be expelled through the new needle 130. It is understood that the device 90 can process any biological material that can be aspirated into the barrel 92. Therefore, the second filter 132 can be selectively chosen based on pore size and the biological material to be excluded from being returned to the patient. In various embodiments, the second filter 132 is selected intra-operatively or pre-operatively.

The present technology also provides methods for processing a biological material, which can be performed at a point of care. The present technology provides methods where the processing of a biological material is performed at a time proximate to administration of the processed biological material. For example, such proximate administration of the processed biological material may be performed 1 hour, 30 minutes, 15 minutes, 10 minutes, 2 minutes, 1 minute, or less, after harvesting the biological material from a patient. In some processes, the methods are "point of care," wherein the processes of the present technology are performed at a location proximate, such as in the same room (for example, bed side) or otherwise immediately adjacent, to the mammalian subject undergoing treatment. The methods enable laparoscopic preparation of, for example, an autologous protein solution, concentrated bone marrow aspirate, or platelet-rich plasma. In an embodiment, the biological material is autologous to the patient to whom it will be administered The device 10 of FIG. 1 is shown in use in FIGS. 5A-5C. With reference to FIGS. 5A-5C, the method comprises aspirating a biological material 150 from a patient 152, through a filter 28, and into the processing device 10. The processing device 10 comprises a needle 24 removably coupled to an outlet 22 of a syringe barrel 12, the filter 28, and a plunger 30. A plurality of beads 26 are positioned within the barrel 12. The plunger 12 comprises a knob 36 and a paddle assembly 40. Drawing back on the plunger 30 causes the biological material 150 to be aspirated into the barrel 12 of the device 10.

As shown in FIG. 5B, after the biological material 150 has been aspirated into the barrel 12 of the processing device 10, the processing device 10 can be held vertically to force the biological material 150 and beads 26 to settle around the paddle assembly 40. Optionally, the needle 24 can be de-coupled from the outlet 22 of the syringe barrel 12. The outlet is then either left uncovered, or it is covered with a cap to ensure no biological material 150 is lost during processing. The biological material 150 is incubated with the beads 26 for a period of time at a predetermined temperature. The period of time for the incubation can be from about 10 seconds to about 2 hours and the temperature can be about room temperature, or a temperature from between about 25° C. to about 40° C. During the incubation, the biological material 150 is continuously or periodically mixed with the beads 26 by turning the knob 36, which causes the paddle assembly 40 to turn. For longer incubation periods, the biological material 150 is mixed with the beads 26 every 5 or 10 minutes by turning the knob 16. Incubating and mixing the biological material 150 with the beads 26 generates a processed biological material 154.

In FIG. 5C, the needle 24 or a new sterile needle 156 is coupled to the outlet 22. Optionally, a second filter can be placed between the outlet 22 and the needle 24, 156 as described above with reference to FIG. 4C. The needle 24, 156 is then inserted into the patient 152 at or near, for example, a site of inflammation. The method then comprises depressing the plunger 30 to expel the processed biological material 154 through the filter 28, out the needle 24, 156, and into the patient 152. Importantly, the beads 26 cannot pass through the filter 28. As shown in FIG. 5C, depressing the plunger 30 causes the paddle assembly 40 to come in contact with the filter 28 and to be become compressed. When a threshold amount of force is applied, the paddle assembly 40 collapses or breaks, which allows the plunger 30 to be depressed further into the barrel 12 to facilitate administration of more processed biological material 154.

The method can be performed in the treatment of inflammation, osteoarthritis, microfractures, meniscus implants, meniscus transplants, or other orthopedic implants or transplants. Uses further include treating osteolysis resulting from wear debris and inflammation at the site of an artificial joint in a patient. Treating osteolysis due to wear debris at a site of an artificial joint implant in a patient includes administering processed biological material at or proximate to the wear debris at the site of the artificial joint implant. In some embodiments, the processed biological material is injected into a tissue or combined with a graft material or implant.

In some embodiments, the biological material is harvested from a patient at a location different from where the processed biological material will be administered. For example, blood can be harvested from a patient's arm, processed in the device, and then administered at a site of inflammation near the patient's knee. In other embodiments, the biological material is harvested from a patient at a location that is the same as from where the processed biological material will be administered.

Embodiments of the present technology are further illustrated through the following non-limiting examples.

Example 1

Preparing Autologous Protein Solution

A device for processing a biological material, such as device 10 of FIG. 1, is selected. The device comprises a syringe barrel 12 containing polyacrylamide beads 26, a filter 28 positioned at a closed end 20 of the barrel 12, a needle 24 coupled to an outlet 22 on the barrel 12, and a plunger 30 inserted into the barrel 12 through an open end 18, wherein the plunger 30 comprises a paddle assembly 40. The paddle assembly 40 comprises a stem 42 and a plurality of paddles 44.

The needle 24 is inserted into an arm of a patient that has inflammation near a knee, the plunger 30 is drawn back, and blood is aspirated from the patient, through the filter 28, and into the syringe barrel 12. The blood is processed by inverting the device 10, and turning the plunger 30, which causes the paddle assembly 40 to turn and mix the polyacrylamide beads 26 with the blood. The polyacrylamide beads 26 activate components in the blood to generate anti-inflammatory cytokines. The processed blood is an autologous protein solution.

The needle 24 is inserted near the knee at the site of inflammation. Depressing the plunger 30 causes the autologous protein solution to flow out of the syringe barrel 12, through the filter 28, out the needle 24, and into the patient. The polyacrylamide beads 26 are excluded by the filter 28 from entering the patient. Pressing firmly on the plunger 30 causes the paddle assembly 40 to contact the filter 28 and collapse, which enables the plunger 30 to be further depressed to ensure all the autologous protein solution is delivered to the patient.

Example 2

Preparing Concentrated Bone Marrow Aspirate

The device 10 described in Example 1 is selected. The needle 24 is inserted into an intramedullary area of a selected bone. The plunger 30 is drawn back and bone marrow is aspirated from the patient, through the filter 28, and into the syringe barrel 12. The bone marrow aspirate is processed by inverting the device 10, and turning the plunger 30, which causes the paddle assembly 40 to turn and mix the polyacrylamide beads 26 with the bone marrow aspirate. The polyacrylamide beads 26 absorb fluid from the bone marrow aspirate, which results in a processed composition comprising concentrated bone marrow aspirate. The needle 24 is then inserted back into the patient, and the plunger 30 is depressed to administer the concentrated bone marrow aspirate to the patient. The polyacrylamide beads 26 are excluded by the filter 28 from entering the patient. Pressing firmly on the plunger 30 causes the paddle assembly 40 to contact the filter 28 and collapse, which enables the plunger 30 to be further depressed to ensure all the autologous protein solution is delivered to the patient.

Example 3

Preparing Platelet-Rich Plasma

The device 10 described in Example 1 is selected. The needle 24 is inserted into an arm of a patient, the plunger 30 is drawn back, and blood is aspirated from the patient, through the filter 28, and into the syringe barrel 12. The needle 24 is removed from the outlet 22 and the outlet 22 is covered with a cap. The blood is processed by inverting the device 10, and turning the plunger 30, which causes the paddle assembly 40 to turn and mix the polyacrylamide beads 26 with the blood. The polyacrylamide beads 26 activate components in the blood to generate anti-inflammatory cytokines.

The cap is removed from the outlet 22, and a second filter, which has a pore size smaller than red blood cells, but larger than platelets, is coupled to the outlet. A new needle is coupled to the filter. The needle is inserted into the patient. Depressing the plunger 30 causes the processed blood to flow out the filter 28, through the second filter, through the needle, and into the patient. Because the second filter excludes red blood cells, platelet-rich plasma is administered to the patient. The polyacrylamide beads 26 are excluded by the filter 28 in the syringe barrel 12 from entering the patient. Pressing firmly on the plunger 30 causes the paddle assembly 40 to become compressed between the plunger 30 and the filter 28 and collapse, which enables the plunger 30 to be further depressed to ensure all the platelet-rich plasma is delivered to the patient.

Example 4

Preparing M2 Macrophages

The device 10 described in Example 1 is selected. The needle 24 is inserted into an arm of a patient, the plunger 30 is drawn back, and blood comprising macrophages is aspirated from the patient, through the filter 28, and into the syringe barrel 12. The blood comprising macrophages is processed by inverting the device 10, and turning the plunger 30, which causes the paddle assembly 40 to turn and mix the polyacrylamide beads 26 with the blood. Contact with the polyacrylamide beads 26 causes the macrophages to polarize into an anti-inflammatory M2 phenotype.

The needle 24 is inserted into a site of inflammation in the patient. Depressing the plunger 30 causes the M2 macrophages to flow out of the syringe barrel 12, through the filter 28, out the needle 24, and into the patient. The polyacrylamide beads 26 are excluded by the filter 28 from entering the patient. Pressing firmly on the plunger 30 causes the paddle assembly 40 to become compressed between the plunger 30 and the filter 28 and collapse, which enables the plunger 30 to be further depressed to ensure all the M2 macrophages are delivered to the patient.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for processing a biological material comprising:
   a syringe barrel having an inner diameter symmetrical about a longitudinal axis, an open end, a closed end, and an outlet at the closed end;
   desiccating beads positioned within the syringe barrel;
   a filter positioned at the closed end of the syringe barrel; and
   a plunger insertable into the syringe barrel through the open end, the plunger including:
     an exterior potion extending from within the syringe barrel, and
     a paddle assembly completely located within the syringe barrel during use, the paddle assembly configured to break into a plurality of pieces when the plunger is depressed and the paddle assembly is pressed against the filter, the paddle assembly fixed to the plunger and located between the plunger and the filter,
   wherein the paddle assembly is configured to mix the biological material with the desiccating beads.

2. The device of claim 1, wherein the beads comprise polystyrene, polyacrylamide, glass, or metal.

3. The device of claim 2, wherein the beads are polyacrylamide beads.

4. The device of claim 1, wherein the filter comprises pores with diameters smaller than the beads.

5. The device of claim 4, wherein the pores are larger than a diameter of the biological material.

6. The device of claim 1, wherein the paddle assembly comprises a stem that extends along the longitudinal axis of the syringe barrel and a plurality of paddles extending radially from the stem.

7. The device of claim 1, wherein the device is configured to withdraw the biological material from a patient, process the biological material, and return the processed biological material back to the patient.

8. The device of claim 7, wherein process the biological material comprises concentrating the biological material.

9. The device of claim 8, wherein the biological material is whole blood, bone marrow, adipose tissue, or chondrocytes.

10. The device of claim 7, wherein the biological material is whole blood comprising macrophages, and contact with the beads induces the macrophages to polarize into an M2 phenotype.

11. The device of claim 1, wherein the filter is positioned within the syringe barrel at the closed end or outside the syringe barrel at the outlet.

12. A device for processing a biological material comprising:
    a syringe barrel extending along a longitudinal axis from an open end to a closed end, and having an outlet at the closed end, wherein polyacrylamide beads are positioned within the syringe barrel;
    a filter positioned at the closed end of the syringe barrel, wherein the filter allows biological materials to pass through, but not the polyacrylamide beads;
    a plunger insertable into the syringe barrel through the open end, the plunger having a paddle assembly, wherein the paddle assembly comprises a stem that extends along the longitudinal axis of the syringe barrel and a plurality of paddles that extend radially from the stem, the stem configured to break into a plurality of pieces when the plunger is depressed and the paddle assembly is pressed against the filter; and a needle, wherein the device is configured to aspirate a biological material from a patient, process the biological material, and return the processed biological material back to the patient.

13. The device of claim 12, wherein the biological material is bone marrow aspirate, the polyacrylamide beads concentrate the bone marrow aspirate to yield concentrated bone marrow aspirate, and concentrated bone marrow aspirate is expelled from the device when the plunger is depressed.

14. The device of claim 12, wherein the biological material is whole blood, adipose tissue, or a combination thereof, and wherein an autologous protein solution is generated when the whole blood, adipose tissue, or combination thereof is contacted with the polyacrylamide beads.

15. The device of claim 12, wherein the filter is positioned inside the syringe barrel at the closed end.

16. The device according to claim 15, further comprising a second filter removably coupled outside the syringe barrel to the outlet.

17. The device of claim 12, wherein the plurality of paddles are configured to break into a plurality of pieces when the plunger is depressed and the paddle assembly is pressed against the filter.

18. A device for processing a biological material comprising:

a syringe barrel having an inner diameter symmetrical about a longitudinal axis, an open end, a closed end, and an outlet at the closed end;

desiccating beads positioned within the syringe barrel, each of the desiccating beads having a diameter;

a filter positioned within the syringe barrel at the closed end, the filter defining pores having diameters that are smaller than the diameter of each of the desiccating beads; and a plunger insertable into the syringe barrel through the open end, the plunger including a paddle assembly configured to collapse and break into a plurality of pieces when the plunger is depressed and the paddle assembly is pressed against the filter, the paddle assembly fixed to the plunger, wherein the paddle assembly is configured to mix the biological material with the desiccating beads when the plunger and paddle assembly are rotated within the syringe barrel.

19. The device of claim 18, wherein the beads comprise at least one of polystyrene, polyacrylamide, glass, or metal.

20. The device of claim 18, wherein the diameters of the pores are larger than a diameter of the biological material.

21. The device of claim 18, wherein the paddle assembly comprises a stem that extends along the longitudinal axis of the syringe barrel and a plurality of paddles extending radially from the stem.

22. The device of claim 18, wherein the device is configured to withdraw the biological material from a patient, process the biological material, and return the processed biological material back to the patient.

* * * * *